US012758538B2

(12) United States Patent
Stirk et al.

(10) Patent No.: US 12,758,538 B2
(45) Date of Patent: Oct. 13, 2026

(54) CRYSTALLINE FORMS OF APALUTAMIDE

(71) Applicant: Apotex Inc., Toronto (CA)

(72) Inventors: Alexander J. Stirk, Brantford (CA); Fabio E. S. Souza, Brantford (CA); Avedis Karadeolian, Brantford (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 292 days.

(21) Appl. No.: 18/717,760

(22) PCT Filed: Nov. 29, 2022

(86) PCT No.: PCT/CA2022/051746
§ 371 (c)(1),
(2) Date: Jun. 7, 2024

(87) PCT Pub. No.: WO2023/102645
PCT Pub. Date: Jun. 15, 2023

(65) Prior Publication Data

US 2025/0049774 A1 Feb. 13, 2025

(30) Foreign Application Priority Data

Dec. 8, 2021 (CA) ................................ CA 3141320

(51) Int. Cl.
*A61K 31/4439* (2006.01)
*A61K 47/10* (2017.01)
*A61K 47/14* (2017.01)

(52) U.S. Cl.
CPC .......... *A61K 31/4439* (2013.01); *A61K 47/10* (2013.01); *A61K 47/14* (2013.01)

(58) Field of Classification Search
CPC .................................................. A61K 31/4439
USPC ........................................................... 514/341
See application file for complete search history.

(56) References Cited

U.S. PATENT DOCUMENTS

| | | | | |
|---|---|---|---|---|
| 9,271,961 | B2 * | 3/2016 | Penning | A61K 31/205 |
| 11,066,384 | B2 | 7/2021 | Chen et al. | |

FOREIGN PATENT DOCUMENTS

| | | | |
|---|---|---|---|
| CN | 110590740 | A | 12/2019 |
| CN | 112679468 | A | 4/2021 |
| IN | 201741043701 | A | 6/2019 |
| IN | 201841030693 | A | 2/2020 |
| IN | 201841038834 | A | 4/2020 |
| IN | 201941022909 | A | 12/2020 |
| WO | 2013184681 | A1 | 12/2013 |
| WO | 2016124149 | A1 | 8/2016 |
| WO | 2018112001 | A1 | 6/2018 |
| WO | 2019016747 | A1 | 1/2019 |
| WO | 2019135254 | A1 | 7/2019 |
| WO | 2020049598 | A1 | 3/2020 |
| WO | 2020188399 | A1 | 9/2020 |
| WO | 2020234817 | A1 | 11/2020 |
| WO | 2021033098 | A1 | 2/2021 |
| WO | 2021048067 | A1 | 3/2021 |
| WO | 2021117062 | A1 | 6/2021 |

OTHER PUBLICATIONS

"CHMP Assessment Report: Erleada", European Medicines Agency, EMEA/H/C/004452/0000, 2018, pp. 1-139.
Childs et al., "Formulation of a Danazol Cocrystal with Controlled Supersaturation Plays an Essential Role in Improving Bioavailability", Mol. Pharmaceutics, 2013, pp. 3112-3127, vol. 10.
Guo et al., "Pharmaceutical cocrystals: A review of preparations, physicochemical properties and applications", Acta Pharmaceutica Sinica B 2021, pp. 2537-2564, vol. 11, No. 8.
Hughes, "Review of Synthetic Routes and Crystalline Forms of the Antiandrogen Oncology Drugs Enzalutamide, Apalutamide, and Darolutamide", Organic Process Research & Development, 2020, pp. 347-362, vol. 24, No. 3.
Martin et al., "Ketoconazole!p!aminobenzoic Acid Cocrystal: Revival of an Old Drug by Crystal Engineering", Molecular Pharmaceutics, 2020, pp. 919-932, vol. 17, No. 3.
Porter, "Coating of Pharmaceutical Dosage Forms", Remington The Science and Practice of Pharmacy 21st Edition; Lippincott Williams & Wilkins: Philadelphia, 2006, Chapter 46.
Rudnic et al., "Oral Solid Dosage Forms", Remington The Science and Practice of Pharmacy 21st Edition; Lippincott Williams & Wilkins: Philadelphia, 2006, Chapter 45.
Sheldrick, "A short history of SHELX", Acta Cryst. A., 2008, pp. 112-122, vol. 64.
Sheldrick, "SHELXT—Integrated space-group and crystal-structure determination", Acta Cryst A., 2015, pp. 3-8, vol. 71.

* cited by examiner

*Primary Examiner* — Niloofar Rahmani
(74) *Attorney, Agent, or Firm* — The Webb Law Firm

(57) ABSTRACT

The present disclosure provides crystalline forms of apalutamide. Specific crystalline forms provided by the disclosure include apalutamide Form APO-I, a cocrystal solvate of apalutamide, vanillin, and n-butyl acetate; apalutamide Form APO-II, a cocrystal solvate of apalutamide, ethylvanillin, and n-butyl acetate; apalutamide Form APO-III, a cocrystal of apalutamide and 4-aminobenzoic acid; and apalutamide Form APO-IV, a cocrystal of apalutamide and vanillin. Also provided are pharmaceutical compositions including the apalutamide crystalline forms and the use of these forms in the treatment of prostate cancer, and in particular metastatic and non-metastatic castration-resistant prostate cancer.

19 Claims, 9 Drawing Sheets

CRYSTALLINE FORMS OF APALUTAMIDE

CROSS-REFERENCE TO RELATED APPLICATIONS

This application is the United States national phase of International Patent Application No. PCT/CA2022/051746 filed Nov. 29, 2022, and claims priority to Canadian Patent Application No. CA 3,141,320 filed Dec. 8, 2021, the disclosures of each of which are hereby incorporated by reference in their entireties.

BACKGROUND

Technical Field

The present disclosure is directed to crystalline forms of apalutamide, pharmaceutical compositions comprising these forms, and their use in the treatment of prostate cancer.

TECHNICAL CONSIDERATIONS

Apalutamide (1), or (4-[7-(6-cyano-5-trifluoromethylpyridin-3-yl)-8-oxo-6-thioxo-5,7-diazaspiro[3.4]oct-5-yl]-2-fluoro-N-methylbenzamide), is the active ingredient in ERLEADA®, which is indicated for the treatment of metastatic castration-sensitive prostate cancer (mCSPC) and non-metastatic castration-resistant prostate cancer (nmCRPC).

(1)

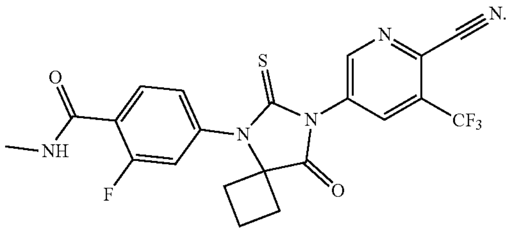

Crystalline forms of apalutamide, including hydrated, solvated, and cocrystal forms thereof, are reported in, for example, WO 2013/184681 A1, WO 2016/124149 A1, WO 2018/112001 A1, WO 2019/016747 A1, IN 201741043701 A, WO 2019/135254 A1, U.S. Pat. No. 11,066,384 B2, IN 201841030693 A, WO 2020/049598 A1, IN 201841038834 A, WO 2020/188399 A1, WO 2020/234817 A1, IN 201941022909 A, WO 2021/033098 A1, WO 2021/048067 A1, WO 2021/117062 A1, CN 110590740 A, and CN 112679468 A.

According to the European CHMP Assessment Report for ERLEADA® (EMEA/H/C/004452/0000), the drug substance synthesis process is reported to afford apalutamide as Form B. In the report, the drug substance is described as having low, pH-independent aqueous solubility but high permeability, placing it in Class II of the Biopharmaceutics Classification System (BCS). Generally, in the case of solid oral dosage forms of Class II drug substances, the limiting factor controlling drug absorption and bioavailability is adequate solubilization of the drug in the aqueous environment of the gastrointestinal tract. As such, improvements in aqueous solubility of the drug substance can be directly correlated with improved drug effectiveness.

Approaches to improving the solubility of a drug substance include, for example, particle size reduction techniques, dispersion of the drug substance onto an inert carrier, and formulation of the drug substance together with solubilizing excipients. For example, WO 2016/090098 A1 describes pharmaceutical formulations comprising a solid dispersion of apalutamide and hydroxypropyl methylcellulose acetate succinate (HPMCAS), which is believed to be used in the ERLEADA® drug product. However, processes for the manufacture of solid dispersion formulations, such as hot melt extrusion, requires specialized equipment and can be operationally complex to implement.

One important measure of the solubility of a drug substance is intrinsic dissolution rate (IDR), which is the dissolution rate of a substance under constant surface area conditions. For low solubility substances such as apalutamide that are classified as BCS Class II, higher IDR values can correlate with higher bioavailability following administration.

Different crystalline forms of the same compound may have different packing, thermodynamic, spectroscopic, kinetic, surface, and mechanical properties. For example, different crystalline forms may have different stability properties. A particular crystalline form may be more sensitive to heat, relative humidity (RH) and/or light. Alternatively or additionally, a particular crystalline form may have different compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Additionally, the particular solubility characteristics of a given crystalline form in relation to undesired impurities can result in differences in the chemical purity of different crystalline forms upon isolation. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more cohesive, more resistant to flow, less capable of dispersing static charge, or may be more difficult to filter and/or wash.

There exists a need for crystalline forms of apalutamide having improved properties for use in providing drug products containing apalutamide, and commercially amenable processes for their manufacture.

SUMMARY

The apalutamide crystalline forms of the present disclosure comprise apalutamide cocrystallized with an aromatic coformer selected from one of 4-aminobenzoic acid, vanillin, or ethylvanillin. Embodiments of crystalline forms comprising vanillin and ethylvanillin further comprise solvated n-butyl acetate. Vanillin, ethylvanillin, and n-butyl acetate are flavorants commonly used in the food industry and 4-aminobenzoic acid is sold as a nutritional supplement. As such, it is expected that these compounds can be safely used in materials intended for use in the preparation of pharmaceutical compositions intended for administration to humans or animals.

Fortuitously, a crystalline form of apalutamide of the present disclosure exhibits higher IDR values compared to not only Form B of apalutamide but also compared to the amorphous form. Further, crystalline forms of the present disclosure exhibit form stability at high temperature and high humidity. Finally, crystalline forms of the present disclosure can be prepared by processes using Class 3 solvents established by the ICH (International Council for Harmonisation of Technical Requirements for Pharmaceuticals for Human Use) as having low toxicity.

Accordingly, in a first embodiment of the present disclosure, there is provided a crystalline form of apalutamide comprising apalutamide and vanillin. In a preferred embodiment of the first embodiment, the molar ratio of apalutamide to vanillin is approximately 1:0.5. In a first preferred embodiment of the first embodiment, the crystalline form further comprises n-butyl acetate. More preferably, the molar ratio of apalutamide to vanillin to n-butyl acetate in this embodiment is approximately 1:0.5:0.5. Preferably, the crystalline form of this embodiment is characterized by a PXRD diffractogram comprising peaks, expressed in degrees 2θ (±0.2°), at 4.3°, 5.5°, and 12.9°. More preferably, the crystalline form of this embodiment is characterized by a PXRD diffractogram further comprising at least three peaks, expressed in degrees 2θ (±0.2°), selected from the group consisting of: 8.6°, 10.9°, 15.3°, 16.0°, 18.7°, and 19.0°. More preferably, the PXRD diffractogram of this embodiment further comprises peaks, expressed in degrees 2θ (±0.2°), at 8.6°, 10.9°, 15.3°, 16.0°, 18.7°, and 19.0°. Preferably, the crystalline form of this embodiment provides a PXRD diffractogram comprising peaks in substantially the same positions (±0.2° 2θ) as those shown in FIG. 1. The crystalline form of this embodiment is preferably characterized by a DSC thermogram comprising an endothermic peak with a peak onset at approximately 92° C. and a peak maximum at approximately 97° C. Preferably, the crystalline form of this embodiment is characterized by a DSC thermogram that is substantially the same in appearance as the DSC thermogram provided in FIG. 5. In a second preferred embodiment of the first embodiment, the crystalline form is characterized by a PXRD diffractogram comprising peaks, expressed in degrees 2θ (±0.2°), at 5.3°, 6.0°, and 9.2°. More preferably, the crystalline form of this embodiment is characterized by a PXRD diffractogram further comprising at least three peaks, expressed in degrees 2θ (+) 0.2°, selected from the group consisting of: 4.6°, 7.8°, 10.3°, 11.6°, 13.6°, and 20.5°. More preferably, the PXRD diffractogram of this embodiment further comprises peaks, expressed in degrees 2θ (±0.2°), at 4.6°, 7.8°, 10.3°, 11.6°, 13.6°, and 20.5°. Preferably, the crystalline form of this embodiment provides a PXRD diffractogram comprising peaks in substantially the same positions (±0.2° 2θ) as those shown in FIG. 4. The crystalline form of this embodiment is preferably characterized by a DSC thermogram comprising an endothermic peak with a peak onset at approximately 114° C. and a peak maximum at approximately 120° C. Preferably, the crystalline form of this embodiment is characterized by a DSC thermogram that is substantially the same in appearance as the DSC thermogram provided in FIG. 8.

In a second embodiment of the present disclosure, there is provided a crystalline form of apalutamide comprising apalutamide and ethylvanillin. In a preferred embodiment of the second embodiment, the molar ratio of apalutamide to ethylvanillin is approximately 1:0.5. In a preferred embodiment of the second embodiment, the crystalline form further comprises n-butyl acetate. More preferably, the molar ratio of apalutamide to ethylvanillin to n-butyl acetate is approximately 1:0.5:0.5. Preferably, the crystalline form of the second embodiment is characterized by a PXRD diffractogram comprising peaks, expressed in degrees 2θ (±0.2°), at 4.3°, 5.5°, and 12.8°. More preferably, the crystalline form of the second embodiment is characterized by a PXRD diffractogram further comprising at least three peaks, expressed in degrees 2θ (±0.2°), selected from the group consisting of: 8.2°, 8.6°, 11.0°, 14.9°, 15.3°, and 16.4°. More preferably, the PXRD diffractogram of this embodiment further comprises peaks, expressed in degrees 2θ (±0.2°), at 8.2°, 8.6°, 11.0°, 14.9°, 15.3°, and 16.4°. Preferably, the crystalline form of the second embodiment provides a PXRD diffractogram comprising peaks in substantially the same positions (±0.2° 2θ) as those shown in FIG. 2. The crystalline form of the second embodiment is preferably characterized by a DSC thermogram comprising an endothermic peak with a peak onset at approximately 104° C. and a peak maximum at approximately 109° C. Preferably, the crystalline form of this embodiment is characterized by a DSC thermogram that is substantially the same in appearance as the DSC thermogram provided in FIG. 6.

In a third embodiment of the present disclosure, there is provided a crystalline form of apalutamide comprising apalutamide and 4-aminobenzoic acid. In a preferred embodiment of the third embodiment, the molar ratio of apalutamide to 4-aminobenzoic acid is approximately 1:1. Preferably, the crystalline form of the third embodiment is characterized by a PXRD diffractogram comprising peaks, expressed in degrees 2θ (±0.2°), at 4.2°, 6.7°, and 16.6°. More preferably, the crystalline form of the third embodiment is characterized by a PXRD diffractogram further comprising at least three peaks, expressed in degrees 2θ (±0.2°), selected from the group consisting of: 8.3°, 9.8°, 15.5°, 18.9°, 23.5°, and 25.8°. More preferably, the PXRD diffractogram of this embodiment further comprises peaks, expressed in degrees 2θ (±0.2°), at 8.3°, 9.8°, 15.5°, 18.9°, 23.5°, and 25.8°. Preferably, the crystalline form of the third embodiment provides a PXRD diffractogram comprising peaks in substantially the same positions (±0.2° 2θ) as those shown in FIG. 3. The crystalline form of the third embodiment is preferably characterized by a DSC thermogram comprising an endothermic peak with a peak onset at approximately 166° C. and a peak maximum at approximately 167° C. Preferably, the crystalline form of this embodiment is characterized by a DSC thermogram that is substantially the same in appearance as the DSC thermogram provided in FIG. 7.

In a fourth embodiment of the present disclosure, there is provided a pharmaceutical composition comprising a crystalline form of apalutamide according to the first, second, or third embodiments of the disclosure, and one or more pharmaceutically acceptable excipients. Preferably, the pharmaceutical composition is in the form of a capsule or a tablet. Preferably, the pharmaceutical composition of the fourth embodiment is a tablet that comprises an amount of the apalutamide crystalline form of the first, second, or third embodiments that is equivalent to 60 mg of apalutamide.

In a fifth embodiment of the present disclosure, there is provided the use of a crystalline form of apalutamide according to the first, second, or third embodiments of the disclosure, or the pharmaceutical composition of the fourth embodiment of the disclosure, in the treatment of prostate cancer. In a preferred embodiment of the fourth embodiment, the prostate cancer is metastatic or non-metastatic castration-resistant prostate cancer.

Other non-limiting aspects, embodiments, and features of the present disclosure will become apparent to those ordinarily skilled in the art upon review of the following description of specific non-limiting embodiments of the disclosure in conjunction with the accompanying figures.

BRIEF DESCRIPTION OF THE DRAWINGS

The terms Fig., Figs., Figure, and Figures are used interchangeably in the specification to refer to the corresponding figures in the drawings. Non-limiting embodiments of the present disclosure are described, by way of example only, with reference to the attached Figure.

DETAILED DESCRIPTION

Figure 1:
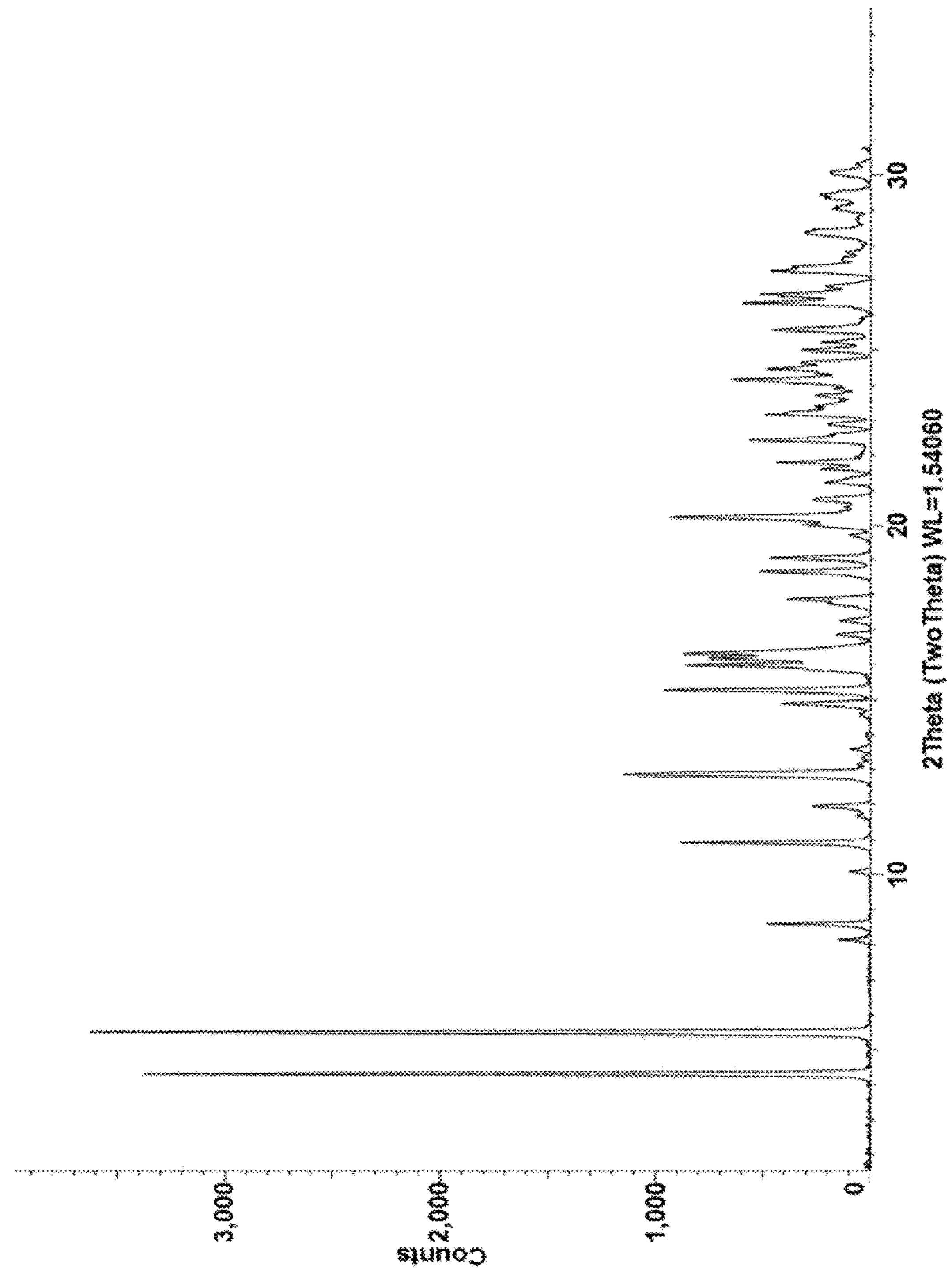
FIG. 1 is a representative PXRD diffractogram of apalutamide Form APO-I as prepared in Example 2.

The apalutamide crystalline forms of the present disclosure comprise apalutamide crystallized together with a coformer selected from one of 4-aminobenzoic acid, vanillin, or ethylvanillin. Crystalline forms comprising vanillin or ethylvanillin further comprising solvated n-butyl acetate are provided. Importantly, with respect to the use of these crystalline forms in the preparation of pharmaceutical compositions, each of 4-aminobenzoic acid, vanillin, ethylvanillin, and n-butyl acetate are included in the U.S. Food & Drug Administration's (FDA's) Substances Added to Food inventory (formerly Everything Added to Food in the United States (EAFUS)). Vanillin and ethylvanillin are also listed in the FDA's Inactive Ingredient Database (IID). The EAFUS list contains ingredients added directly to food that the FDA has either approved as food additives, or has listed or affirmed as being GRAS (Generally Recognized As Safe). The IID list provides information on inactive ingredients present in FDA-approved drug products. Once an inactive ingredient has appeared in an approved drug product for a particular route of administration, the inactive ingredient is not considered new, and may require a less extensive review the next time it is included in a new drug product.

Also, of importance to the present disclosure is that a crystalline form of the disclosure exhibits higher IDR compared to both Form B of apalutamide as well as the amorphous form. Due to the classification of apalutamide as a BCS Class II substance having low solubility but high permeability, provision of a crystalline form of apalutamide having an improved dissolution rate could equate to an increase in bioavailability.

The apalutamide crystalline forms of the present disclosure exhibit differences in properties when compared to the known crystalline forms of apalutamide. Properties that differ between the disclosure and known crystalline forms of apalutamide include, but are not limited to, crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tabletting, handling, flow, and/or blending.

Further, crystalline forms of the present disclosure can be prepared via processes that use Class 3 solvents established by the ICH (International Council for Harmonisation of Technical Requirements for Pharmaceuticals for Human Use) as having low toxicity.

Depending on the manner in which the crystalline forms of the present disclosure are prepared, and the methodology and instrument used for PXRD analysis, the intensity of a given peak observed in a PXRD diffractogram of the crystalline form may vary when compared to the same peak in the representative PXRD diffractograms provided in FIGS. 1 to 4. Thus, differences in relative peak intensities between peaks in a PXRD diffractogram for a given crystalline form may be observed when compared to the relative peak intensities of the peaks in the representative PXRD diffractograms of FIGS. 1 to 4. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the disclosure herein.

In addition to the differences in relative peak intensities that may be observed in comparison to the representative PXRD diffractograms provided in FIGS. 1 to 4, it is understood that individual peak positions may vary between ±0.2° 2θ from the values observed in the representative PXRD diffractograms provided in FIGS. 1 to 4 for the crystalline forms of the disclosure, or listed in Tables 1 to 4. Such variations are known and understood by a person of skill in the art, and any such variations do not depart from the disclosure herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 4. Thus, PXRD diffractograms of the crystalline forms of the present disclosure may, in some circumstances, display the same relative peak positions as observed in the representative PXRD diffractograms provided in FIGS. 1 to 4, with the exception that each peak is offset in the same direction, and by approximately the same amount, such that the overall PXRD diffractogram is substantially the same in appearance as the PXRD diffractograms of FIGS. 1 to 4, with the exception of the uniform offset in peak positions. The observation of any such uniform peak shift in a PXRD diffractogram does not depart from the disclosure herein given that the relative peak positions of the individual peaks within the PXRD diffractogram remain consistent with the relative peak positions observed in the PXRD diffractograms of FIGS. 1 to 4.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermograms provided in FIGS. 5 to 8 and described herein. Such variations are known and understood by a person of skill in the art, and any such variations do not depart from the disclosure herein.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms. Single-component forms of apalutamide, such as those known in the art, consist solely of apalutamide in the repeating unit of the crystal lattice. Multiple-component forms of apalutamide, such as those of the present disclosure, include crystalline forms of apalutamide wherein one or more other molecules, including a coformer and/or a solvent molecule, are also incorporated into the crystal lattice with apalutamide.

Multi-component crystalline forms comprising more than one type of molecule in the crystalline lattice may have some variability in the exact molar ratio of their components depending on the conditions used for their preparation. For example, a molar ratio of components within a multi-component crystalline form provides a person of skill in the art information as to the general relative quantities of the components of the crystalline form. In many cases, the molar ratio may vary by ±25% from a stated range. With respect to the present disclosure, a molar ratio of 1:1 should be understood to include the ratios 1:0.75 and 1:1.25, as well as all of the individual ratios in between.

As used herein, the term "room temperature" refers to a temperature in the range of 20° C. to 25° C.

As used herein, "vanillin" refers to 4-hydroxy-3-methoxybenzaldehyde and "ethylvanillin" refers to 3-ethoxy-4-hydroxybenzaldehyde.

When describing the non-limiting embodiments of the present disclosure there may be a common variance to a given temperature or time that would be understood or expected by the person skilled in the art to provide substantially the same result. For example, when reference is made to a particular temperature, it is to be understood by the person skilled in the art that there is an allowable variance of +5° C. associated with that temperature. When reference is made to a particular time, it is to be understood that there is an allowable variance of +10 minutes when the time is one or two hours, and +1 hour when longer periods of time are referenced.

In one embodiment of the present disclosure, there is provided a new crystalline form of apalutamide, apalutamide Form APO-I, a hemi-vanillin cocrystal, hemi-n-butyl acetate solvate. Preferably, in apalutamide Form APO-I, the molar ratio of apalutamide to vanillin to n-butyl acetate is approximately 1:0.5:0.5.

Apalutamide Form APO-I can be characterized by a PXRD diffractogram comprising, among other peaks, characteristic peaks, expressed in degrees 2θ (±0.2°), at 4.3°, 5.5° and 12.9°. Preferably, the PXRD diffractogram further comprises at least three peaks, expressed in degrees 2θ (±0.2°), selected from the group consisting of 8.6°, 10.9°, 15.3°, 16.0°, 18.7°, and 19.0°. More preferably, the PXRD diffractogram further comprises peaks, expressed in degrees 2θ (±0.2°), at 8.6°, 10.9°, 15.3°, 16.0°, 18.7°, and 19.0°.

An illustrative PXRD diffractogram of apalutamide Form APO-I, as prepared in Examples 1 and 2, is shown in FIG. 1. A peak listing, comprising representative peaks from the PXRD diffractogram in FIG. 1, and their relative intensities, is provided in Table 1. Although illustrative of the PXRD diffractogram that is provided for the apalutamide Form APO-I of the present disclosure, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Apalutamide Form APO-I from FIG. 1

| Angle (2θ) | Relative intensity (%) |
|---|---|
| 4.31 | 92.5 |
| 5.51 | 100.0 |
| 8.60 | 13.3 |
| 10.92 | 25.7 |
| 12.87 | 32.1 |
| 14.90 | 11.9 |
| 15.28 | 28.7 |
| 15.99 | 24.8 |
| 16.18 | 21.8 |
| 16.32 | 25.8 |
| 17.86 | 11.6 |
| 18.66 | 15.0 |
| 19.04 | 13.8 |
| 20.25 | 28.2 |
| 21.61 | 7.4 |
| 22.44 | 17.9 |
| 25.57 | 14.3 |

Figure 5:
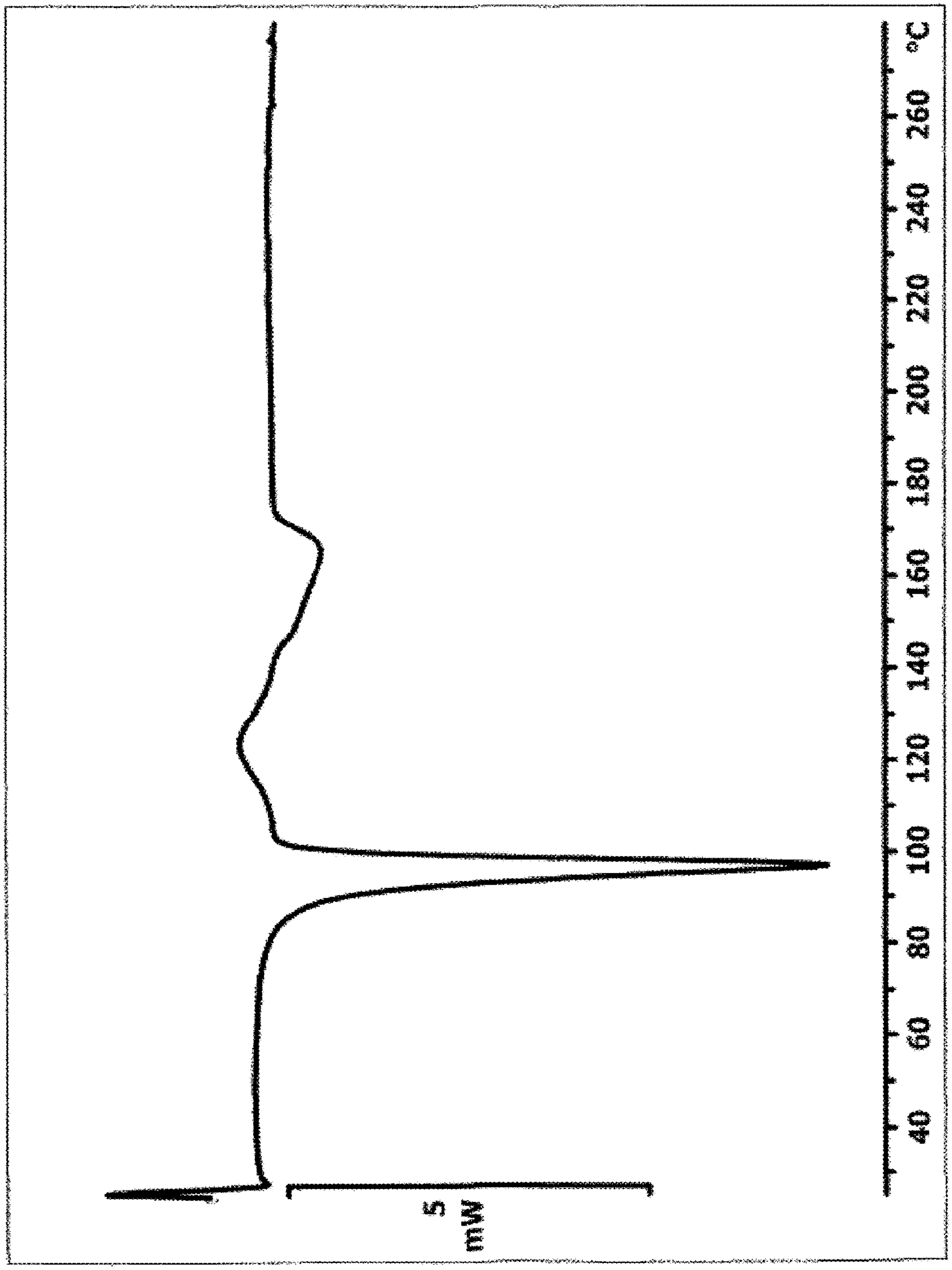
FIG. 5 is a representative DSC thermogram of apalutamide Form APO-I as prepared in Example 2.

An illustrative DSC thermogram of apalutamide Form APO-I is shown in FIG. 5. The DSC thermogram may be further characterized by an endothermic peak with a peak onset at approximately 92° C. and a peak maximum at approximately 97° C.

As described in Examples 1 and 2, apalutamide Form APO-I can be prepared by combining apalutamide with an approximately equimolar amount of vanillin in the presence of n-butyl acetate, preferably affording a solution, to which is added a suitable anti-solvent, preferably heptane, affording a suspension. After a suitable time, the resulting suspension is isolated and dried, if necessary, preferably in vacuo and at an elevated temperature, preferably in the range of approximately 30° C. and approximately 50° C. to afford apalutamide Form APO-I having a PXRD diffractogram consistent with FIG. 1.

Figure 9:
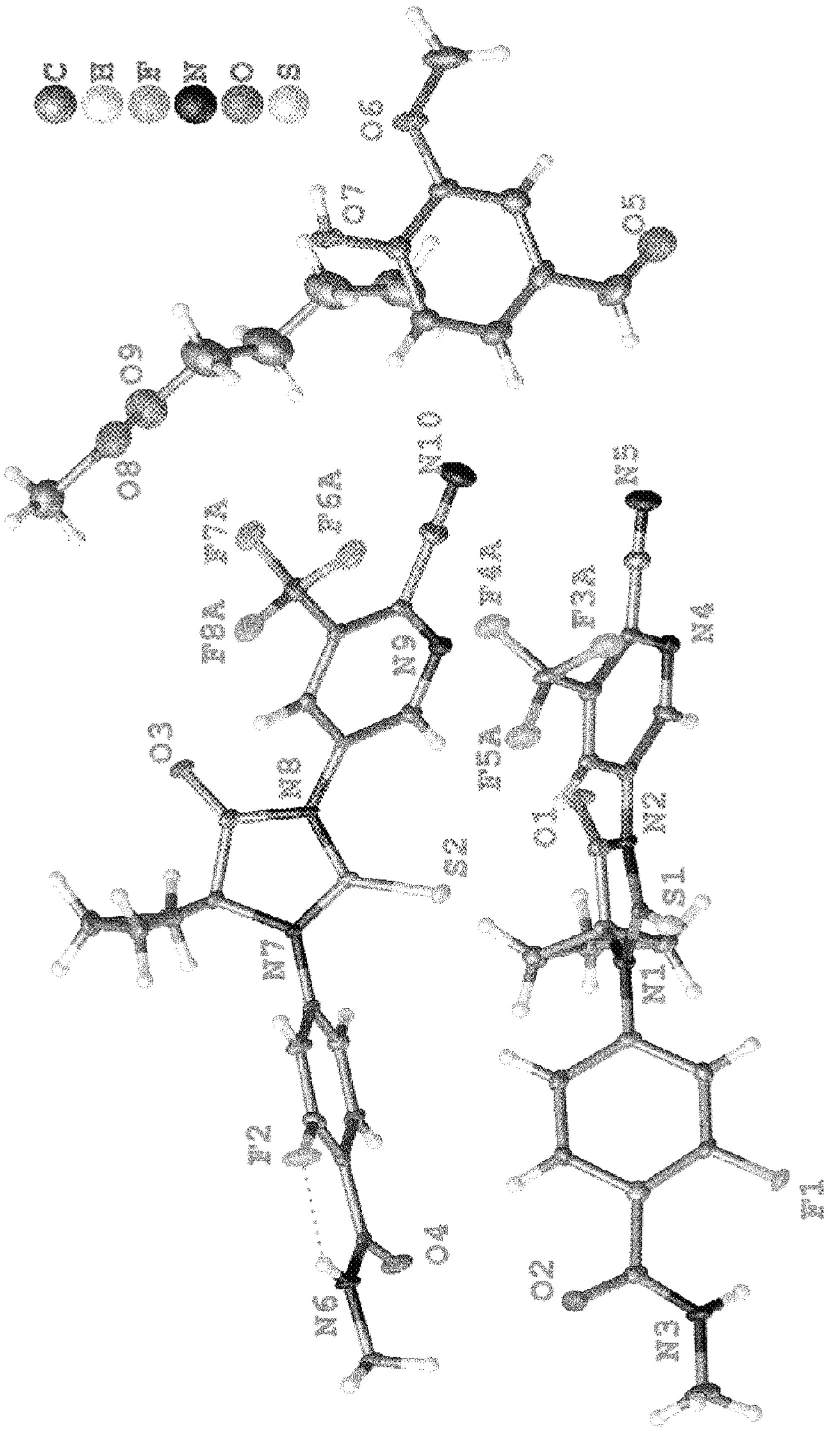
FIG. 9 is an illustration of the SCXRD of apalutamide Form APO-I.

Single crystals of apalutamide Form APO-I were grown from slow vapour diffusion of heptane into a solution of n-butyl acetate, apalutamide, and vanillin as described in Example 8 and characterized by SCXRD. A summary of the SCXRD data is provided in Table 2. An illustration of the unit cell from the SCXRD structure is shown in FIG. 9. This illustration depicts a 1:0.5:0.5 apalutamide:vanillin:n-butyl acetate cocrystal solvate, i.e., the molar ratio of apalutamide to vanillin to n-butyl acetate is 1:0.5:0.5.

TABLE 2

Single crystal X-ray diffraction parameters of apalutamide form APO-I

| | |
|---|---|
| Formula | $C_{56}H_{50}F_8N_{10}O_9S_2$ |
| Formula Weight, g $mol^{-1}$ | 1223.18 |
| Crystal System | Triclinic |
| Space Group | P-1 |
| Collection Temperature, K | 149.99 |
| a, Å | 7.8891(5) |
| b, Å | 17.4505(11) |
| c, Å | 22.2374(15) |
| α, ° | 67.254(3) |
| β, ° | 82.828(4) |
| γ, ° | 82.553(4) |
| V, $Å^3$ | 2790.1(3) |
| Z | 2 |
| ρ, g $cm^{-3}$ | 1.456 |
| λ, Å, (MoKα) | 0.71073 |
| 2θ range for data collection, ° | 3.774 to 50 |
| Unique reflections measured/reflections included in refinement | 9833 |
| $R_1$ | 0.0915 |

TABLE 2-continued

| Single crystal X-ray diffraction parameters of apalutamide form APO-I | |
|---|---|
| $wR_2$ | 0.1718 |
| $R_1$ (all data) | 0.1079 |
| $wR_2$ (all data) | 0.1789 |
| Goodness of Fit | 1.197 |
| Min & Max peak heights on final ΔF map, eÅ$^{-3}$ | 0.75/−0.65 |

In a second embodiment of the present disclosure, there is provided a new crystalline form of apalutamide, apalutamide Form APO-II, a hemi-ethylvanillin cocrystal, hemi-n-butyl acetate solvate. Preferably, in apalutamide Form APO-II, the molar ratio of apalutamide to ethylvanillin to n-butyl acetate is approximately 1:0.5:0.5. PXRD studies of capped samples of apalutamide Form APO-II maintained in a 40° C./75% RH stability chamber for at least one month showed that no change in the crystalline form occurred.

Apalutamide Form APO-II can be characterized by a PXRD diffractogram comprising, among other peaks, characteristic peaks, expressed in degrees 2θ (±0.2°), at 4.3°, 5.5°, and 12.8°. Preferably, the PXRD diffractogram further comprises at least three peaks, expressed in degrees 2θ (+) 0.2°, selected from the group consisting of 8.2°, 8.6°, 11.0°, 14.9°, 15.3°, and 16.4°. More preferably, the PXRD diffractogram further comprises peaks, expressed in degrees 2θ (±0.2°), at 8.2°, 8.6°, 11.0°, 14.9°, 15.3°, and 16.4°.

Figure 2:
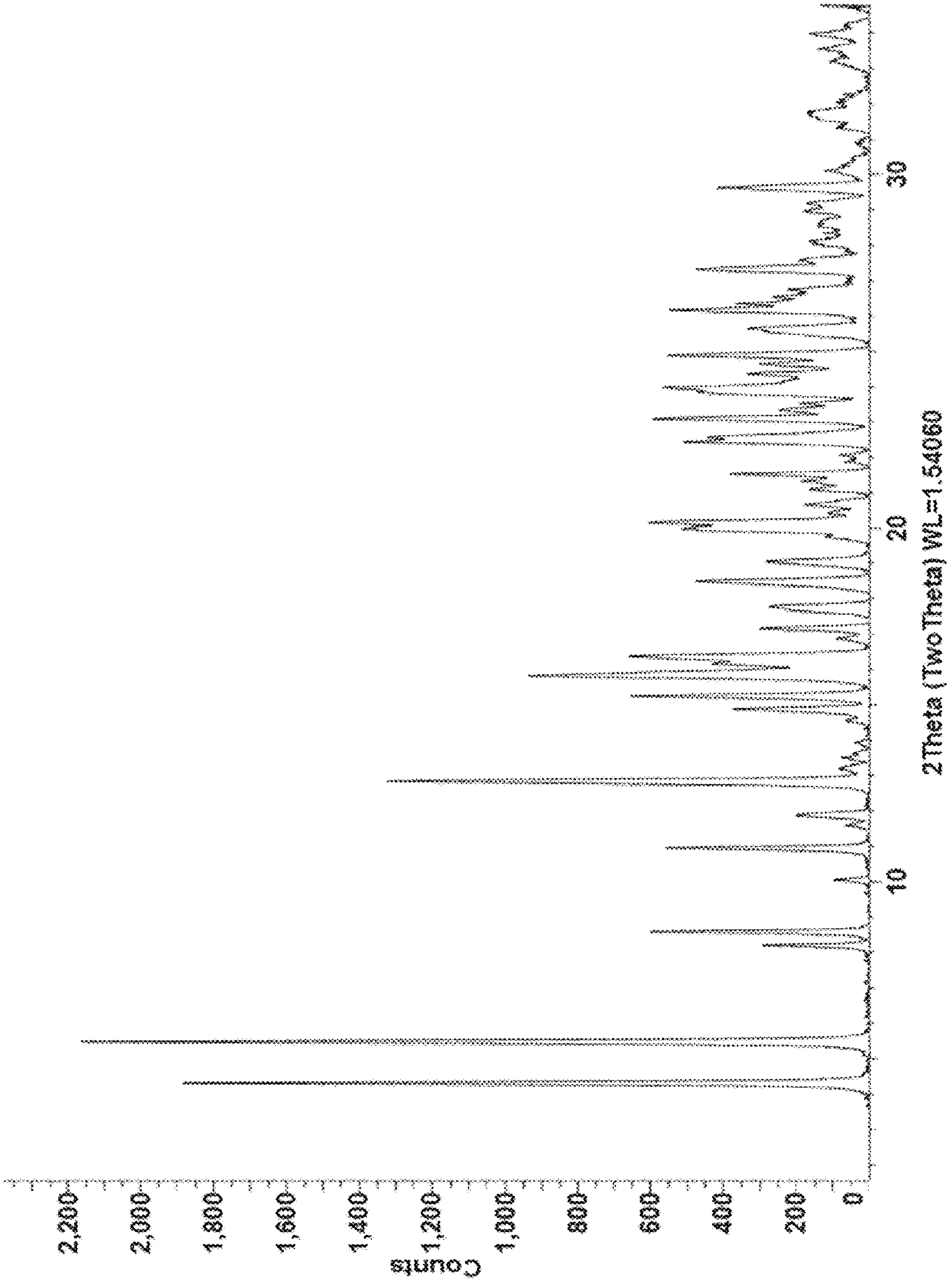
FIG. 2 is a representative PXRD diffractogram of apalutamide Form APO-II as prepared in Example 4.

An illustrative PXRD diffractogram of apalutamide Form APO-II, as prepared in Examples 3 and 4, is shown in FIG. 2. A peak listing, comprising representative peaks from the PXRD diffractogram in FIG. 2, and their relative intensities, is provided in Table 3. Although illustrative of the PXRD diffractogram that is provided for the apalutamide Form APO-II of the present disclosure, the relative intensities of the peaks are variable. Thus, depending on a particular sample, the prominence or relative intensity of the peaks observed may differ from those in the illustrative PXRD diffractogram and peak listing.

TABLE 3

Relative peak intensities of apalutamide Form APO-II from FIG. 2

| Angle (2θ) | Relative intensity (%) |
|---|---|
| 4.32 | 86.5 |
| 5.48 | 100.0 |
| 8.20 | 13.5 |
| 8.58 | 28.4 |
| 10.96 | 26.8 |
| 11.89 | 8.9 |
| 12.84 | 62.4 |
| 14.88 | 17.9 |
| 15.26 | 31.9 |
| 15.82 | 43.7 |
| 16.39 | 31.4 |
| 17.17 | 14.1 |
| 18.49 | 22.6 |
| 19.04 | 13.4 |
| 20.17 | 30.4 |
| 24.89 | 28.7 |

Figure 6:
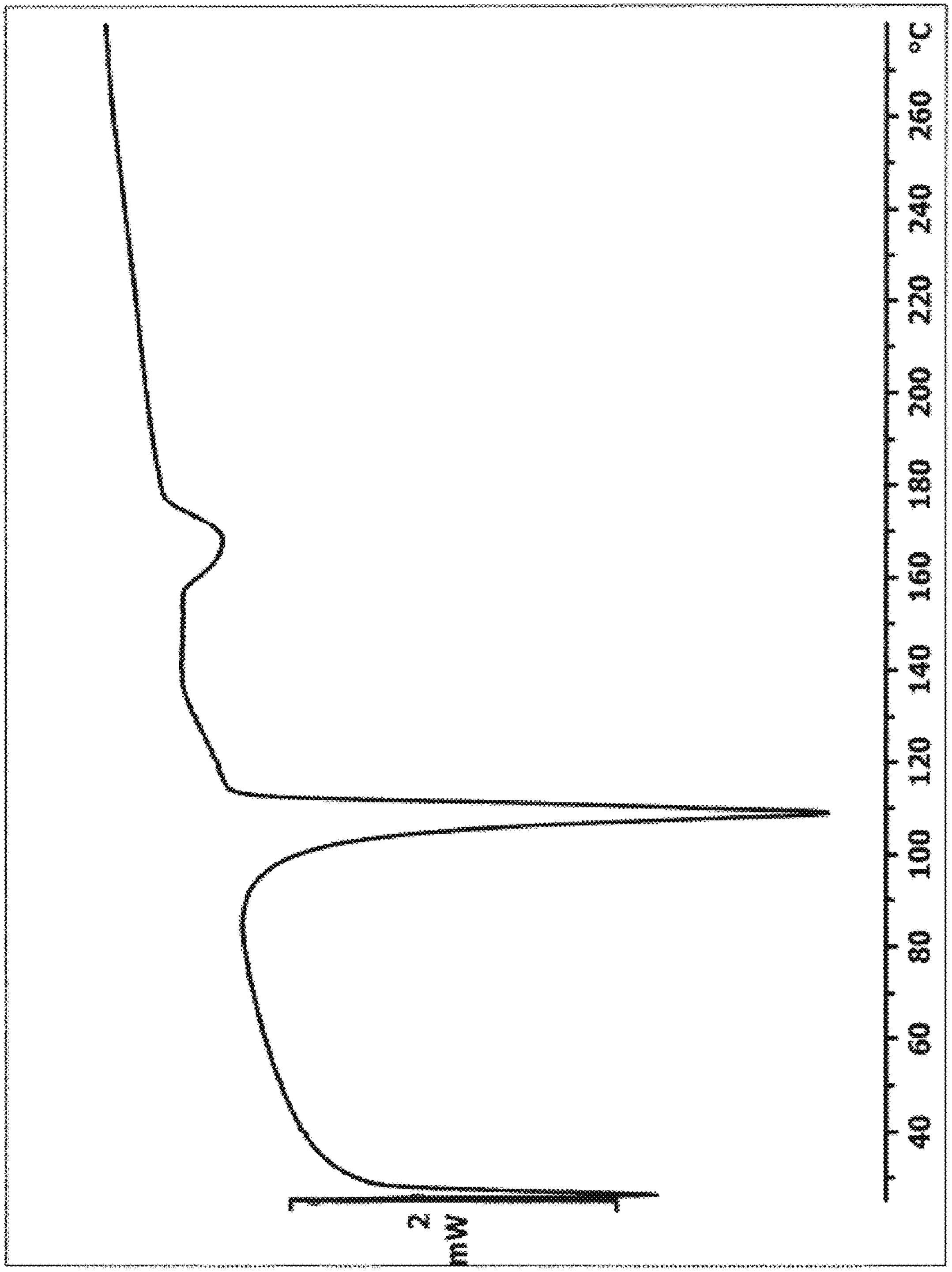
FIG. 6 is a representative DSC thermogram of apalutamide Form APO-II as prepared in Example 4.

An illustrative DSC thermogram of apalutamide Form APO-II is shown in FIG. 6. The DSC thermogram may be further characterized by an endothermic peak with a peak onset at approximately 104° C. and a peak maximum at approximately 109° C.

As described in Examples 3 and 4, apalutamide Form APO-II can be prepared by combining apalutamide with an approximately equimolar amount of ethylvanillin in the presence of n-butyl acetate at an elevated temperature, preferably affording a solution, to which is added a suitable anti-solvent, preferably heptane, affording a suspension. After a suitable time, the resulting suspension is isolated and dried, if necessary, preferably in vacuo and in the range of approximately 25° C. and approximately 50° C. to afford apalutamide Form APO-II having a PXRD diffractogram consistent with FIG. 2.

In a third embodiment of the present disclosure, there is provided a new crystalline form of apalutamide, apalutamide Form APO-III, a 4-aminobenzoic acid cocrystal. Preferably, in apalutamide Form APO-III, the molar ratio of apalutamide to 4-aminobenzoic acid is approximately 1:1.

Apalutamide Form APO-III can be characterized by a PXRD diffractogram comprising, among other peaks, characteristic peaks, expressed in degrees 2θ (±0.2°), at 4.2°, 6.7°, and 16.6°. Preferably, the PXRD diffractogram further comprises at least three peaks, expressed in degrees 2θ (+) 0.2°, selected from the group consisting of 8.3°, 9.8°, 15.5°, 18.9°, 23.5°, and 25.8°. More preferably, the PXRD diffractogram further comprises peaks, expressed in degrees 2θ (±0.2°), at 8.3°, 9.8°, 15.5°, 18.9°, 23.5°, and 25.8°. PXRD studies of capped samples of apalutamide Form APO-III maintained in a 40° C./75% RH stability chamber for at least one month showed that no change in the crystalline form occurred.

Figure 3:
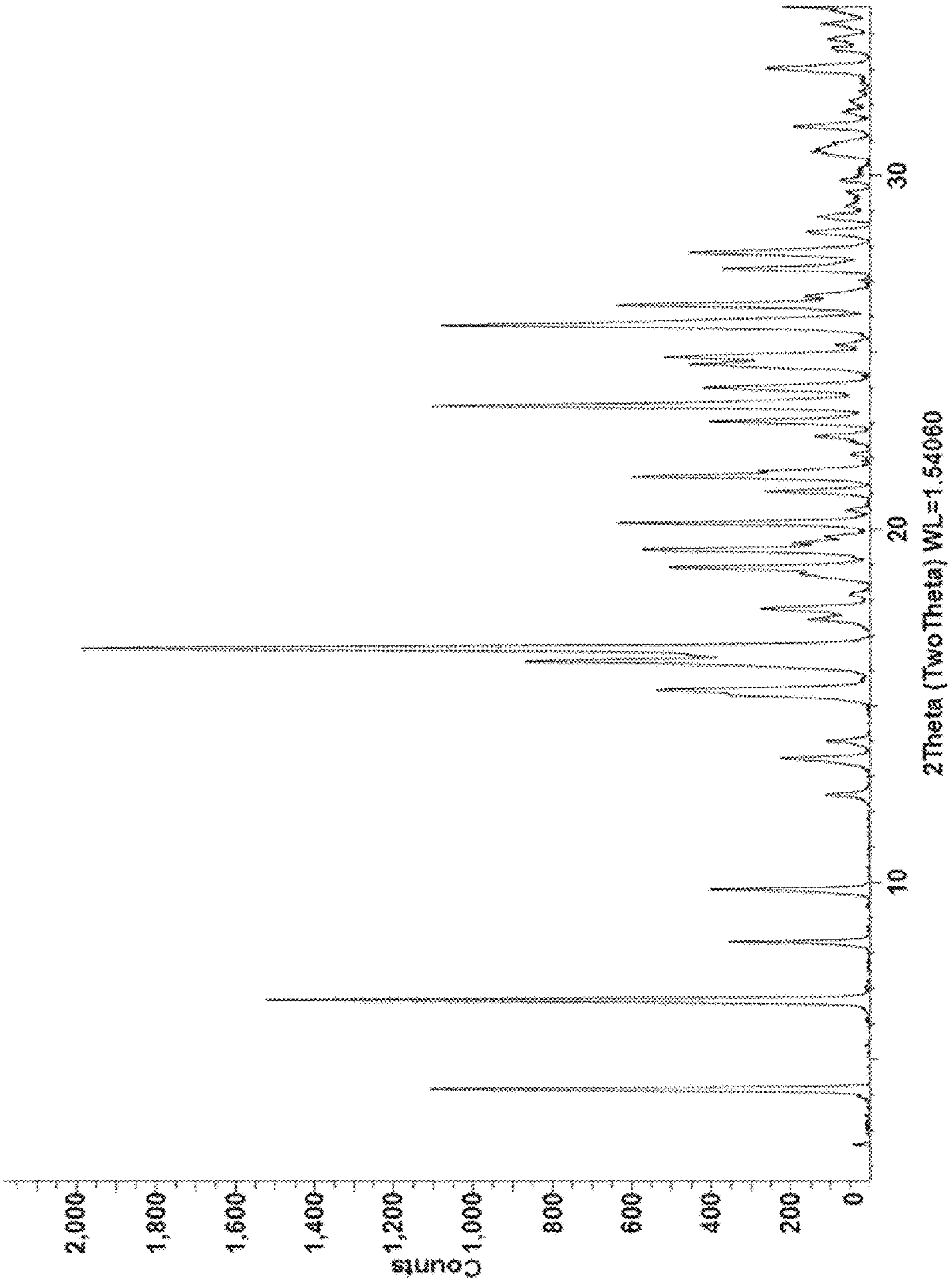
FIG. 3 is a representative PXRD diffractogram of apalutamide Form APO-III as prepared in Example 6.

An illustrative PXRD diffractogram of apalutamide Form APO-III, as prepared in Examples 5 and 6, is shown in FIG. 3. A peak listing, comprising representative peaks from the PXRD diffractogram in FIG. 3, and their relative intensities, is provided in Table 4. Although illustrative of the PXRD diffractogram that is provided for the apalutamide Form APO-III of the present disclosure, the relative intensities of the peaks are variable. Thus, depending on a particular sample, the prominence or relative intensity of the peaks observed may differ from those in the illustrative PXRD diffractogram and peak listing.

TABLE 4

Relative peak intensities of apalutamide Form APO-III from FIG. 3

| Angle (2θ) | Relative intensity (%) |
|---|---|
| 4.17 | 52.1 |
| 6.68 | 72.2 |
| 8.31 | 17.4 |
| 9.81 | 19.6 |
| 13.53 | 10.8 |
| 15.45 | 26.5 |
| 16.25 | 41.8 |
| 16.64 | 100.0 |
| 17.74 | 13.3 |
| 18.91 | 24.5 |
| 19.41 | 27.5 |
| 20.18 | 33.5 |
| 21.47 | 32.6 |
| 23.48 | 59.2 |
| 25.75 | 58.4 |

Figure 7:
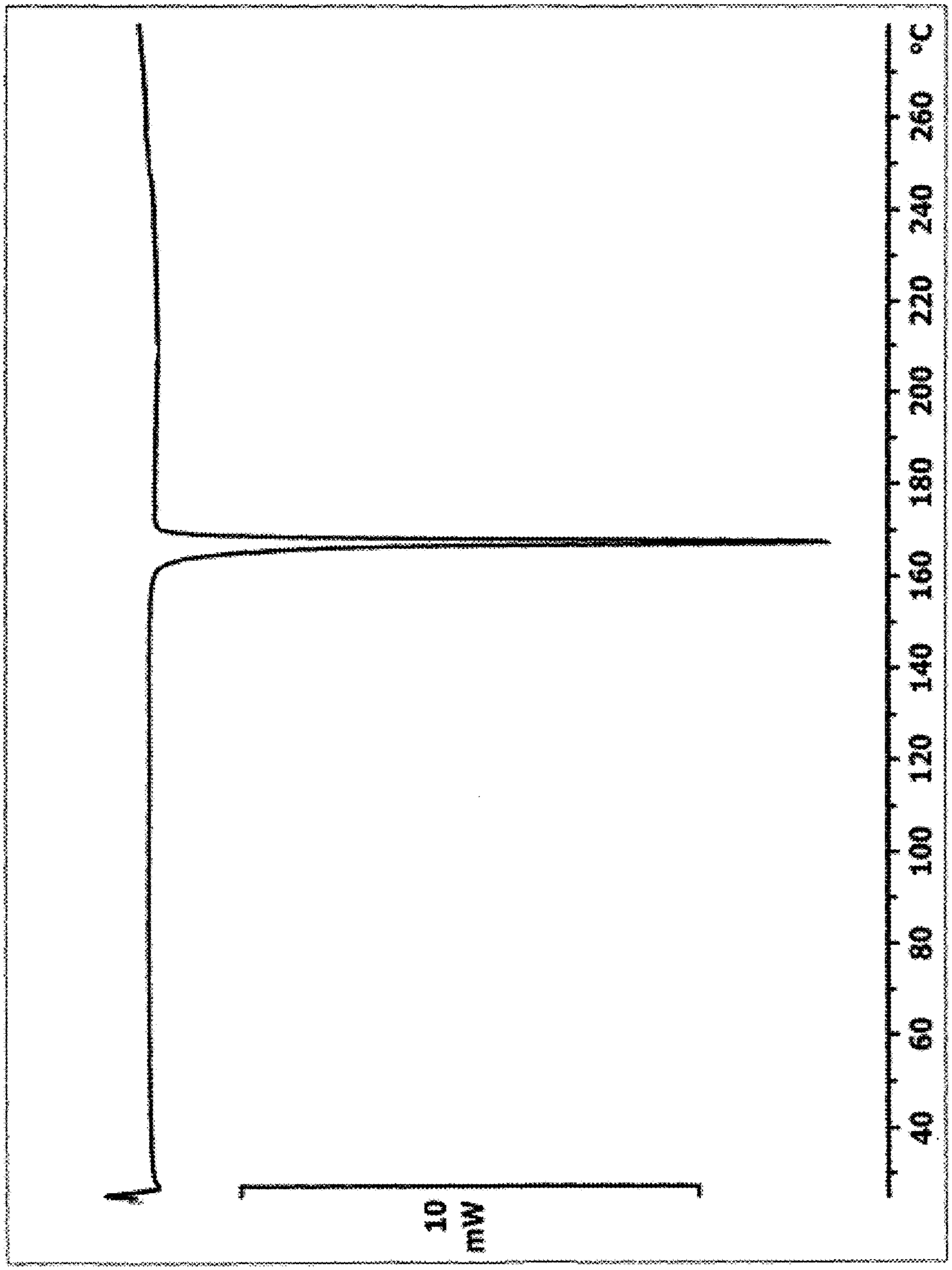
FIG. 7 is a representative DSC thermogram of apalutamide Form APO-III as prepared in Example 6.

An illustrative DSC thermogram of apalutamide Form APO-III is shown in FIG. 7. The DSC thermogram may be further characterized by an endothermic peak with a peak onset at approximately 166° C. and a peak maximum at approximately 167° C.

As described in Examples 5 and 6, apalutamide Form APO-III can be prepared by combining apalutamide with an approximately equimolar amount of 4-aminobenzoic acid in the presence of n-butyl acetate, preferably affording a solution, to which is added a suitable anti-solvent, preferably heptane, affording a suspension. After a suitable time, the resulting suspension is isolated and dried, if necessary, preferably in vacuo and in the range of approximately 30° C. and approximately 50° C. to afford apalutamide Form APO-III having a PXRD diffractogram consistent with FIG. 3.

In a fourth embodiment of the present disclosure, there is provided a new crystalline form of apalutamide, apalutamide Form APO-IV, a hemi-vanillin cocrystal. Preferably, in apalutamide Form APO-IV, the molar ratio of apalutamide to vanillin is approximately 1:0.5.

Apalutamide Form APO-IV can be characterized by a PXRD diffractogram comprising, among other peaks, characteristic peaks, expressed in degrees 2θ (±0.2°), at 5.3°, 6.0°, and 9.2°. Preferably, the PXRD diffractogram further comprises at least three peaks, expressed in degrees 2θ (+) 0.2°, selected from the group consisting of 4.6°, 7.8°, 10.3°, 11.6°, 13.6°, and 20.5°. More preferably, the PXRD diffractogram further comprises peaks, expressed in degrees 2θ (±0.2°), at 4.6°, 7.8°, 10.3°, 11.6°, 13.6°, and 20.5°.

Figure 4:
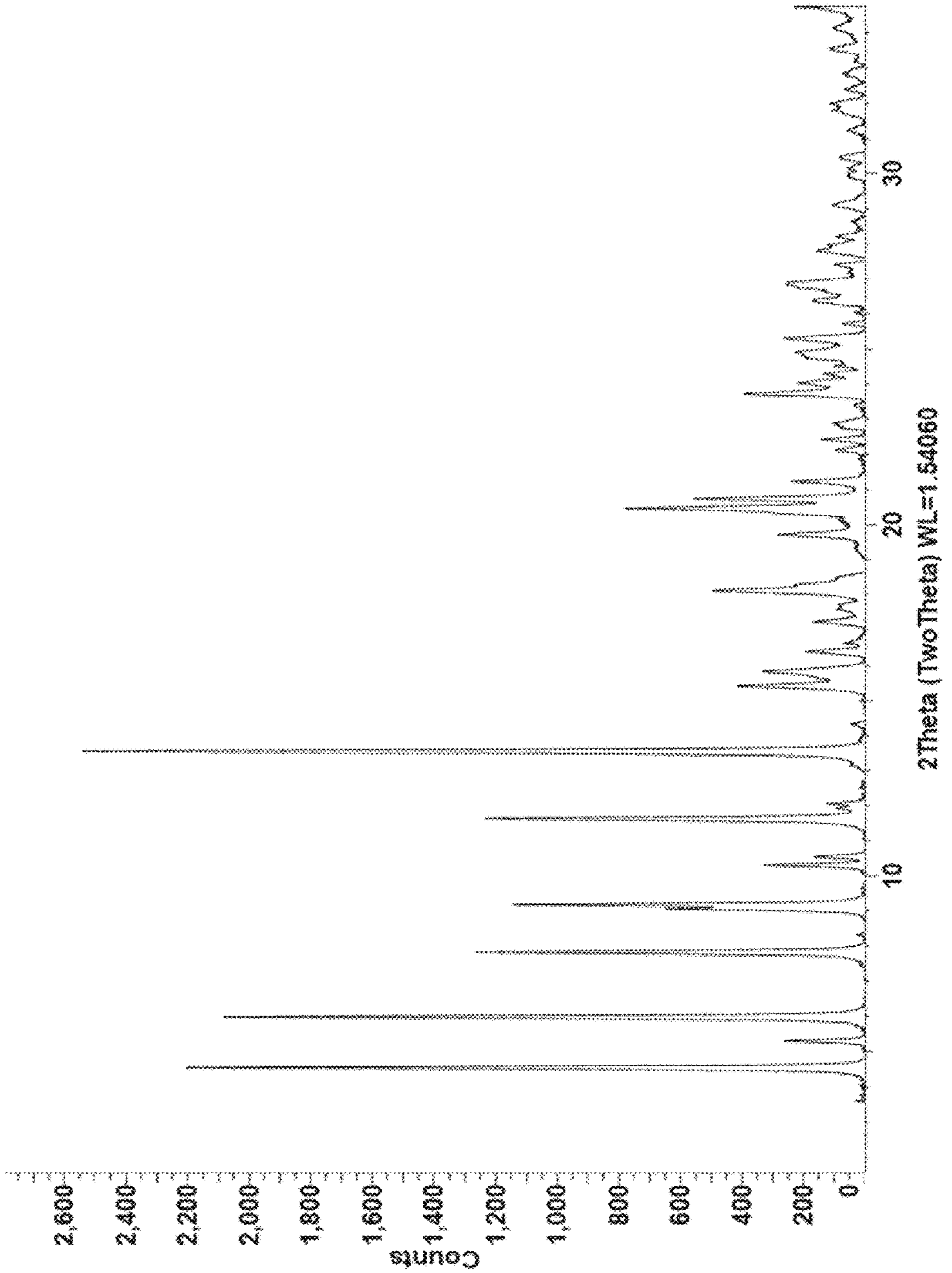
FIG. 4 is a representative PXRD diffractogram of apalutamide Form APO-IV as prepared in Example 7.

An illustrative PXRD diffractogram of apalutamide Form APO-IV, as prepared in Example 7, is shown in FIG. 4. A peak listing, comprising representative peaks from the PXRD diffractogram in FIG. 4, and their relative intensities, is provided in Table 5. Although illustrative of the PXRD diffractogram that is provided for the apalutamide Form APO-IV of the present disclosure, the relative intensities of the peaks are variable. Thus, depending on a particular 10 sample, the prominence or relative intensity of the peaks observed may differ from those in the illustrative PXRD diffractogram and peak listing.

TABLE 5

Relative peak intensities of apalutamide Form APO-IV from FIG. 4

| Angle (2θ) | Relative intensity (%) |
|---|---|
| 4.55 | 83.6 |
| 5.29 | 9.9 |
| 5.98 | 79.3 |
| 7.82 | 48.9 |
| 9.19 | 44.6 |
| 10.32 | 13.1 |
| 11.63 | 47.4 |
| 13.57 | 100.0 |
| 15.42 | 15.9 |
| 15.83 | 12.5 |
| 18.12 | 19.4 |
| 19.71 | 11.3 |
| 20.47 | 32.5 |
| 23.74 | 16.3 |

Figure 8:
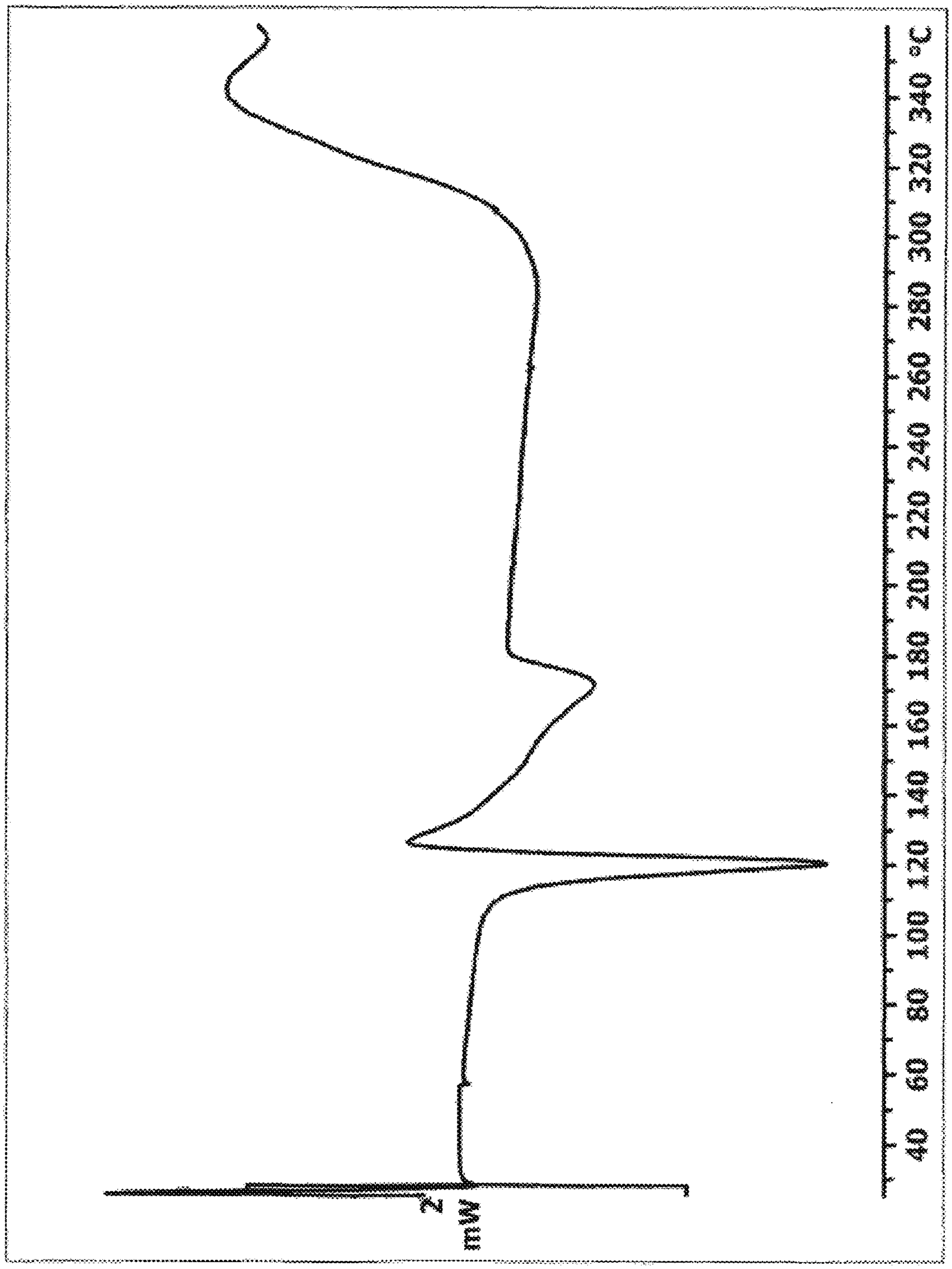
FIG. 8 is a representative DSC thermogram of apalutamide Form APO-IV as prepared in Example 7.

An illustrative DSC thermogram of apalutamide Form APO-IV is shown in FIG. 8. The DSC thermogram may be further characterized by an endothermic peak with a peak onset at approximately 114° C. and a peak maximum at approximately 120° C.

As described in Example 7, apalutamide Form APO-IV can be prepared by exposing apalutamide Form APO-I to warm, moist air, preferably air having a relative humidity of approximately 70% to approximately 80%, at a temperature in the range of approximately 35° C. and approximately 45° C., for a suitable time corresponding with purge of n-butyl acetate, to afford apalutamide Form APO-IV having a PXRD diffractogram consistent with FIG. 4.

In a further embodiment of the disclosure, there is provided a pharmaceutical composition of a crystalline form of apalutamide comprising vanillin, with one or more pharmaceutically acceptable excipients. In another embodiment of the disclosure, there is provided a pharmaceutical composition of a crystalline form of apalutamide comprising vanillin and n-butyl acetate, with one or more pharmaceutically acceptable excipients. In another embodiment of the disclosure, there is provided a pharmaceutical composition of a crystalline form of apalutamide comprising ethylvanillin and n-butyl acetate, with one or more pharmaceutically acceptable excipients. In another embodiment of the disclosure, there is provided a pharmaceutical composition of a crystalline form of apalutamide comprising 4-aminobenzoic acid, with one or more pharmaceutically acceptable excipients. In another embodiment of the disclosure, there is provided a pharmaceutical composition comprising a crystalline form of apalutamide selected from the group consisting of Form APO-I, Form APO-II, Form APO-III, and Form APO-IV. Preferably, the pharmaceutical composition is a solid dosage form suitable for oral administration, such as a capsule, tablet, pill, powder, or granulate. Most preferably, the pharmaceutical composition is a tablet. Preferably, the pharmaceutical composition provides a dose of apalutamide that is equivalent to the 60 mg of apalutamide found in ERLEADA® drug products.

Suitable pharmaceutically acceptable excipients are preferably inert with respect to the crystalline form of apalutamide of the present disclosure, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and/or sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and/or lactitol; disintegrants such as croscarmellose sodium, crospovidone, polyvinylpyrrolidone, sodium starch glycollate, corn starch, microcrystalline cellulose, hydroxypropyl methylcellulose and/or hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and/or talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and/or stearic acid. Other excipients including preservatives, stabilisers, anti-oxidants, silica flow conditioners, antiadherents and/or glidants may be added as required. Other suitable excipients and the preparation of solid oral dosage forms is well known to person of skill in the art, and is described generally, for example, in *Remington The Science and Practice of Pharmacy* $21^{st}$ *Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and/or extended-release coatings, using standard pharmaceutical coatings. Such coatings, and their application, are well known to persons skilled in the art, and are described, for example, in *Remington The Science and Practice of Pharmacy* $21^{st}$ *Edition* (Lippincott Williams & Wilkins: Philadelphia; 2006; Chapter 46).

EXAMPLES

The following non-limiting examples are illustrative of some of the aspects and embodiments of the disclosure herein.

The apalutamide used as a starting material in the following examples was consistent with Form C apalutamide which is reported in WO 2013/184681 A1. However, other polymorphic forms are equally suitable as starting material, provided dissolution of the form occurs when preparing the crystalline form of apalutamide of the present disclosure.

PXRD Analysis:

PXRD diffractograms were recorded on a Bruker D8 Discover powder X-ray diffractometer (Bruker AXS LLC, Karlsruhe, Germany). The generator was a Incoatec Microfocus Source (IμS) Cu tube (λ=1.54060 Å) with a voltage of 50 kV and current of 1.00 mA, using a divergence slit of 0.1 mm and collimator of 2.0 mm. For each sample, two frames were collected using a still scan with a PILATUS3 R 100K-A detector at the distance of 294.2 mm from the sample. Raw data were evaluated using the program DIFFRAC.EVA (Bruker AXS LLC, Karlsruhe, Germany).

Differential Scanning Calorimetry Analysis:

The DSC thermograms were collected on a Mettler-Toledo 821e instrument. Each sample (1-2.5 mg) was weighed into a 40 μL aluminum pan and was crimped closed with an aluminum lid having a 50 μm pinhole. The sample was analyzed under a flow of nitrogen (60±2 mL/min) at a scan rate of 10° C./minute between 25° C. and 280° C.

Single Crystal Data Collection and Processing

A single crystal was mounted on a cryoloop with paratone oil and examined on a Bruker APEX-II CCD X-ray diffractometer using graphite-monochromated Mo-Kα radiation (λ=0.71073 Å) equipped with a CCD area detector and an Oxford Cryoflex low temperature device. Data was measured at 150 (2) K using the APEX-II software (APEX-II, Bruker AXS Inc. Madison, Wisconsin, USA, 2007). Cell refinement and data-reduction were carried out by SAINT (SAINT, Bruker AXS, Madison, Wisconsin, USA). An absorption correction was performed by the multi-scan method implemented in SADABS (SADABS, Bruker AXS, Madison, Wisconsin, USA; G. M. Sheldrick, SHELXS97 and SHELXL97, University of Göttingen, Germany, 1996). Final cell constants were determined from full least squares refinement of all observed reflections.

Single Crystal Structure Solution and Refinement

The crystal structure was solved by intrinsic phasing SHELXT and refined using SHELXL-2014 in the Bruker SHELXTL suite (G M. Sheldrick, *Acta Cryst.* A. 2008, 64, 112-122; G. M. Sheldrick, *Acta Cryst A.* 2015, 71, 3-8). All structures were refined with full squares refinement on $F^2$ using the SHELXTL software.

Example 1: Preparation Apalutamide Form APO-I

A mixture of apalutamide (0.50 g, 1.05 mmol) and vanillin (0.16 g, 1.05 mmol) in n-butyl acetate (6.0 mL) was stirred at room temperature, producing a clear yellow solution. Heptane (1.0 mL) was added to the solution. After 90 minutes, the thick white solids were collected by filtration and dried in vacuo at 40° C. for 12 hours to afford apalutamide Form APO-I as a white solid (0.24 g).

Example 2: Preparation of Apalutamide Form APO-I

A mixture of apalutamide (1.00 g, 2.10 mmol) and vanillin (0.32 g, 2.10 mmol) in n-butyl acetate (12.0 mL) was stirred at room temperature, producing a clear yellow solution. Heptane (2.0 mL) was added to the solution, following by seeding the solution with apalutamide Form APO-I prepared as in Example 1 (~2 mg). After 2 hours, heptane (1 mL) was added to the thick, white precipitate and the temperature was allowed to reach 19° C. After 40 minutes, the solids were collected by filtration and dried in vacuo at 40° C. for 12 hours to afford apalutamide Form APO-I as a white solid (0.87 g). $^1$H NMR analysis of the solid (DMSO-$d_6$) revealed a molar ratio of apalutamide:vanillin:n-butyl acetate of approximately (1:0.5:0.5). The PXRD diffractogram and DSC thermogram of a sample prepared by this method are shown in FIG. 1 and FIG. 5, respectively.

$^1$H-NMR of apalutamide Form APO-I (DMSO-$d_6$, 300 MHZ) δ: 0.88 (t, J=7.4 Hz, 1.5H), 1.32 (sx, J=7.4 Hz, 1H), 1.47-1.67 (m, 2H), 1.90-2.07 (m, 1H), 1.99 (s, 1.5H), 2.41-2.56 (m, 2H), 2.59-2.71 (m, 2H), 2.80, 2.82 (sx2, 3H), 3.84 (s, 1.5H), 3.99 (t, J=6.6 Hz, 1H), 6.96 (d, J=8.0 Hz, 0.5H), 7.35-7.44 (m, 1.5H), 7.46 (d, J=10.6, 1H), 7.83 (t, J=8.0 Hz), 8.48 (br m, 1H), 8.75 (d, J=1.7 Hz, 1H), 9.21 (s, 1H), 9.77 (s, 0.5H), 10.25 (s, 0.5H).

Example 3: Preparation of Apalutamide Form APO-II

A mixture of apalutamide (0.10 g, 0.21 mmol), ethylvanillin (0.07 g, 0.42 mmol), and n-butyl acetate (1.2 mL) was heated to 45° C. with stirring, producing a clear yellow solution. Following filtration through a 0.45 μm polytetrafluoroethylene (PTFE) frit, heptane (1 mL) was slowly added to the solution. The heating was discontinued, and after 5 minutes, a thick precipitate had formed. The precipitate was filtered and the solid was washed with an ice-cold solution of n-butyl acetate:heptane (1:1, 2 mL), followed by heptane (1 mL), then allowed to dry at room temperature to afford apalutamide Form APO-II as a white solid (0.61 g).

Example 4: Preparation of Apalutamide Form APO-II

A mixture of apalutamide (1.00 g, 2.10 mmol), ethylvanillin (0.35 g, 2.10 mmol), and n-butyl acetate (12.0 mL) was heated to 30° C. with stirring, producing a clear yellow solution. Following filtration through a 0.45 μm polytetrafluoroethylene (PTFE) frit, heptane (3 mL) was slowly added to the solution. The heating was discontinued, and the solution was seeded with apalutamide Form APO-II prepared as in Example 3 (~2 mg). After 1 minute, a thick precipitate had formed. After 30 minutes, the precipitate was filtered and the solid was washed with an ice-cold solution of n-butyl acetate:heptane (1:1, 2 mL) and allowed to dry at room temperature to afford apalutamide Form APO-II as a white solid (0.88 g). $^1$H NMR analysis of the solid (DMSO-$d_6$) revealed a molar ratio of apalutamide:ethylvanillin:n-butyl acetate of approximately (1:0.5:0.5). The PXRD diffractogram and DSC thermogram of a sample prepared by this method are shown in FIG. 2 and FIG. 6, respectively.

$^1$H-NMR of apalutamide Form APO-II (DMSO-$d_6$, 500 MHZ) δ: 0.89 (t, J=7.4 Hz, 1.5H), 1.33 (m, 1H), 1.36 (t, J=7.0 Hz, 1.5H), 1.51-1.64 (m, 2H), 1.94-2.04 (m, 1H), 2.00 (s, 1.5H), 2.46-2.55 (m, 2H), 2.62-2.70 (m, 2H), 2.81, 2.82 (s ×2, 3H), 4.00 (t, J=6.6 Hz, 1H), 4.10 (q, J=7.0 Hz, 1H), 6.97 (d, J=8.1 Hz, 0.5H), 7.37 (d, J=1.9 Hz, 0.5H), 7.39 (dd, J=8.1, 1.8 Hz, 1H), 7.41 (dd, J=Hz, 0.5H), 7.47 (dd, J=10.5, 1.8 Hz, 1H), 7.84 (t, J=8.0 Hz), 8.49 (br m, 1H), 8.76 (d, J=2.0 Hz, 1H), 9.22 (d, J=1.9 Hz, 1H), 9.76 (s, 0.5H), 10.18 (s, 0.5H).

Example 5: Preparation of Apalutamide Form APO-III

A mixture of apalutamide (0.10 g, 0.21 mmol) and 4-aminobenzoic acid (0.03 g, 0.21 mmol) in n-butyl acetate (1.2 mL) was stirred at 45° C., producing a clear yellow solution. Following filtration through a 0.45 μm PTFE frit, heptane (1.0 mL) was added and the heating discontinued. After 3 minutes, a thick white precipitate formed, which was collected by filtration and washed with an ice-cold solution of n-butyl acetate:heptane (1:1, 1 mL) and dried in vacuo at 40° C. for 12 hours to afford apalutamide Form APO-III as a white solid (0.06 g).

Example 6: Preparation of Apalutamide Form APO-III

A mixture of apalutamide (0.50 g, 1.05 mmol) and 4-aminobenzoic acid (0.14 g, 1.05 mmol) in n-butyl acetate (7.0 mL) was stirred at room temperature, producing a clear yellow solution. Following filtration through a 0.45 μm PTFE frit, heptane (5.0 mL) was added and the solution was seeded with apalutamide Form APO-III prepared as in Example 5 (~2 mg). After 1 minute, a thick white precipitate formed, which was collected by filtration and washed with an ice-cold solution of n-butyl acetate:heptane (1:1, 1 mL) and dried in vacuo at 40° C. for 12 hours to afford apalutamide Form APO-III as a white solid (0.31 g). $^1$H NMR analysis of the solid (DMSO-$d_6$) revealed a molar ratio of apalutamide:4-aminobenzoic acid of approximately (1:1). The PXRD diffractogram and DSC thermogram of a sample prepared by this method are shown in FIG. 3 and FIG. 7, respectively.

$^1$H-NMR of apalutamide Form APO-III (DMSO-$d_6$, 300 MHZ) δ: 1.51-1.69 (m, 1H), 1.89-2.08 (m, 1H), 2.43-2.58 (m, 2H), 2.60-2.74 (m, 2H), 2.80, 2.82 (s ×2, 3H), 5.87 (s, 2H), 6.53 (d, J=8.6 Hz, 2H), 7.38 (dd, J=8.1, 1.7 Hz, 1H), 7.47 (dd, J=10.5, 1.7 Hz, 1H), 7.60 (d, J=8.6 Hz, 2H), 7.83 (t, J=8.0 Hz, 1H), 8.48 (br m, 1H), 8.75 (d, J=1.9 Hz, 1H), 9.21 (d, J=1.9 Hz, 1H), 11.94 (s, 1H).

Example 7: Preparation of Apalutamide Form APO-IV

Apalutamide Form APO-I (100 mg) was placed in a 20 mL vial covered with a tissue. The vial was then placed in a chamber at 40° C. and 75% relative humidity. After 2 months, the solid was removed from the chamber to afford apalutamide Form APO-IV. $^1$H NMR analysis of the solid ($CDCl_3$) revealed a molar ratio of apalutamide:vanillin of approximately (1:0.5) and absence of n-butyl acetate. The PXRD diffractogram and DSC thermogram of the solid prepared by this method are shown in FIG. 4 and FIG. 8, respectively.

$^1$H-NMR of apalutamide Form APO-IV ($CDCl_3$, 300 MHZ) δ: 1.65-1.81 (m, 1H), 2.18-2.37 (m, 1H), 2.50-2.65 (m, 2H), 2.67-2.80 (m, 2H), 3.09, 3.10 (s ×2, 3H), 3.98 (s, 1.5H), 6.24 (s, 0.5H), 6.67-6.80 (m, 1H), 7.05 (d, J=8.5 Hz, 0.5H), 7.18 (dd, J=11.5, 1.8 Hz, 1H), 7.27 (dd, J=8.2, 2.0 Hz, 1H), 7.40-7.46 (m, 1H), 8.34 (t, J=8.4 Hz, 1H), 8.36 (d, J=2.1 Hz, 1H), 9.09 (d, J=2.1 Hz, 1H), 9.84 (s, 0.5H).

Example 8: Preparation of Single Crystals of Apalutamide Form APO-I

Needle-like single crystals were obtained by dissolving ~20 mg of apalutamide Form APO-I in n-butyl acetate (50 μL) and slowly diffusing heptane via vapour over three weeks. Suitable crystals were removed from the solvent and analysed via SCXRD. FIG. 9 depicts an illustration of the SCXRD of the apalutamide Form APO-I crystals prepared by this method. PXRD of a portion of the crystals was consistent with that shown in FIG. 1.

Example 9: Comparative Intrinsic Dissolution Testing

Intrinsic dissolution rate (IDR) measurements were performed using a Wood's apparatus. Samples were prepared by compressing an amount (approximately 200 mg) of sample at 1.5 metric tons for 1 minute. A dissolution medium consisting of 900 ml distilled water maintained at 37° C., and rotation speed of 50 rpm, was used for each experiment. Results are provided in Table 6.

TABLE 6

Comparative intrinsic dissolution rates for the crystalline form of the disclosure with crystalline form B of apalutamide described in WO 2013/184681 A1 and amorphous form

| Form | Intrinsic Dissolution Rate (mg min$^{-1}$ cm$^{-2}$) |
|---|---|
| Apalutamide Form B (Prior Art) | 0.0065 |
| Apalutamide Amorphous Form (Prior Art) | 0.0085 |
| Apalutamide Form APO-I | 0.0222 |

What is claimed is:

1. A crystalline form of apalutamide comprising apalutamide and vanillin.

2. The crystalline form of claim 1, wherein the molar ratio of apalutamide to vanillin is approximately 1:0.5.

3. The crystalline form of claim 2, wherein the crystalline form further comprises n-butyl acetate.

4. The crystalline form of claim 3, wherein the molar ratio of apalutamide to vanillin to n-butyl acetate is approximately 1:0.5:0.5.

5. The crystalline form of apalutamide of claim 4, characterized by a PXRD diffractogram comprising peaks, expressed in degrees 2θ (±0.2°), at 4.3°, 5.5°, and 12.9°.

6. The crystalline form of claim 5, further comprising at least three peaks, expressed in degrees 2θ (±0.2°), selected from the group consisting of: 8.6°, 10.9°, 15.3°, 16.0°, 18.7°, and 19.0°.

7. The crystalline form of claim 5, further comprising peaks, expressed in degrees 2θ (±0.2°), at 8.6°, 10.9°, 15.3°, 16.0°, 18.7°, and 19.0°.

8. The crystalline form of claim 4, providing a PXRD diffractogram comprising peaks in substantially the same positions (±0.2° 2θ) as those shown in FIG. 1.

9. The crystalline form of claim 5, characterized by a DSC thermogram comprising an endothermic peak with a peak onset at approximately 92° C. and a peak maximum at approximately 97° C.

10. The crystalline form of claim 5, characterized by a DSC thermogram that is substantially the same in appearance as the DSC thermogram provided in FIG. 5.

11. The crystalline form of apalutamide of claim 2, characterized by a PXRD diffractogram comprising peaks, expressed in degrees 2θ (±0.2°), at 5.3°, 6.0°, and 9.2°.

12. The crystalline form of claim 11, further comprising at least three peaks, expressed in degrees 2θ (±0.2°), selected from the group consisting of: 4.6°, 7.8°, 10.3°, 11.6°, 13.6°, and 20.5°.

13. The crystalline form of claim 11, further comprising peaks, expressed in degrees 2θ (±0.2°), at 4.6°, 7.8°, 10.3°, 11.6°, 13.6°, and 20.5°.

14. The crystalline form of claim 4, providing a PXRD diffractogram comprising peaks in substantially the same positions (±0.2° 2θ) as those shown in FIG. 4.

15. The crystalline form of claim 11, characterized by a DSC thermogram comprising an endothermic peak with a peak onset at approximately 114° C. and a peak maximum at approximately 120° C.

16. The crystalline form of claim 11, characterized by a DSC thermogram that is substantially the same in appearance as the DSC thermogram provided in FIG. 8.

17. A pharmaceutical composition comprising a crystalline form of apalutamide according to claim 4, and one or more pharmaceutically acceptable excipients.

18. The pharmaceutical composition of claim 17, wherein the pharmaceutical composition is a capsule or a tablet.

19. The pharmaceutical composition of claim 18, wherein the pharmaceutical composition is a tablet.

* * * * *